(12) United States Patent
Boulangé et al.

(10) Patent No.: US 11,879,858 B2
(45) Date of Patent: Jan. 23, 2024

(54) METHOD FOR IDENTIFYING THE LITHOLOGICAL LAYER OF AN EXCAVATED MATERIAL FOR THE PURPOSE OF ITS VALORISATION

(71) Applicant: EIFFAGE GC INFRA LINEAIRES, Velizy-Villacoublay (FR)

(72) Inventors: Laurence Boulangé, Chapareillan (FR); Florian Doom, Montévrain (FR); Matthieu Jeannelle, Saint Broingt les Fosses (FR)

(73) Assignee: EIFFAGE GC INFRA LINEAIRES, Velizy-Villacoublay (FR)

( * ) Notice: Subject to any disclaimer, the term of this patent is extended or adjusted under 35 U.S.C. 154(b) by 45 days.

(21) Appl. No.: 17/690,398

(22) Filed: Mar. 9, 2022

(65) Prior Publication Data
US 2022/0291154 A1    Sep. 15, 2022

(30) Foreign Application Priority Data
Mar. 10, 2021    (FR) ....................... 2102346

(51) Int. Cl.
*G01N 23/223*    (2006.01)
*G01N 33/24*    (2006.01)

(52) U.S. Cl.
CPC .......... *G01N 23/223* (2013.01); *G01N 33/24* (2013.01); *G01N 2223/616* (2013.01)

(58) Field of Classification Search
CPC ................. G01N 23/223; G01N 33/24; G01N 2223/616; G01N 2223/076
See application file for complete search history.

(56) References Cited

U.S. PATENT DOCUMENTS

2018/0238774 A1* 8/2018 Amendt ................. G01N 33/24
2021/0215590 A1   7/2021 Li et al.

FOREIGN PATENT DOCUMENTS

| CN | 102944570 A | * | 2/2013 |
| FR | 3062917 A1 | | 8/2018 |
| WO | 2020/199292 A1 | | 10/2020 |

OTHER PUBLICATIONS

Sabri et al., Chemical and Structural Analysis of Rocks Using X-ray Fluorescence and X-ray Diffraction Techniques, Jun. 12, 2020, The Scientific Journal of Koya University, pp. 79-87. (Year: 2020).*
Povarov et al., Quantification of total element concentrations in soils using total x-ray fluorescence spectroscopy, Sep. 15, 2023, ACS Omega, vol. 6, 24595-24601. (Year: 2021).*
Towett et al., Quantification of total element concentrations in soils using total X-ray fluorescence spectroscopy (TXRF), Jul. 3, 2013, Science of the Total Environment, pp. 374-388 (Year: 2013).*
French Search Report dated Oct. 22, 2021 in corresponding application No. 2102346; 18 pgs.
Ross P.-S. et al.: "Improving lithological discrimination in exploration drill-cores using portable X-ray fluorescence measurements: (1) testing three Olympus Innov-X analysers on unprepared cores", Geochemistry: Exploration, Environment, Analysis, vol. 14, No. 2, Feb. 4, 2014, pp. 171-185, 23 pges.

* cited by examiner

*Primary Examiner* — Christine S. Kim
(74) *Attorney, Agent, or Firm* — Maier & Maier, PLLC

(57) ABSTRACT

A method for quickly and reliably identifying the lithological layer of an excavated material, which includes the steps of: a) analysing a specimen of the excavated material using X-ray fluorescence spectroscopy to determine the mass concentration of each of the inorganic chemical elements contained in the specimen, step a) being performed on n different surfaces of the specimen in order to determine n mass concentrations of each of the inorganic chemical elements contained in the specimen, with n being a whole number greater than or equal to 2, b) calculating the mean of the n mass concentrations of each of the inorganic chemical elements contained in the specimen and the standard deviation of this mean, c) classifying each of the inorganic chemical elements contained in the excavated material according to certain criteria for the mean n mass concentration, and d) identifying the lithological layer of the excavated material based on the classification performed during step c).

12 Claims, No Drawings

METHOD FOR IDENTIFYING THE LITHOLOGICAL LAYER OF AN EXCAVATED MATERIAL FOR THE PURPOSE OF ITS VALORISATION

FIELD

The present invention relates to the field of valorisation of excavated materials as a building material, in particular as backfill or aggregate.

BACKGROUND

During large civil engineering projects, and in particular when digging tunnels, a very large amount of excavated material is generated in a very short period of time, requiring a considerable area of ground on the construction sites. For example, a tunnelling machine used to construct an underground railway line extracts approximately 800 tonnes a day of excavated material.

Conventionally, the excavated material is stored in waste storage facilities which take up a very large area of ground. In order to overcome this problem, one solution consists in valorising this excavated material as new building materials.

The excavated material contains numerous different inorganic chemical elements which over time can impair the properties of these new building materials and adversely affect the structures in which they are used. For this reason, the mass concentration of inorganic chemical elements in an excavated material must be determined before deciding if and how it should be valorised.

However, it is not enough just to determine the mass concentration of inorganic chemical elements. Indeed, two excavated materials can have the same composition of inorganic chemical elements but have different geomechanical and chemical properties according to their lithological layer. For this reason, it is also necessary to identify the lithological layer of the excavated material before deciding if and how it should be valorised.

Currently, the lithological layer of an excavated material is determined by X-ray diffraction analysis. This method of analysis allows the crystalline structure of each crystalline phase that forms part of the excavated material to be defined so that the lithological layer of the excavated material can then be identified. However, this method of analysis takes several days to complete and requires highly skilled people to interpret the diffractograms. It also requires the analysis specimens to be prepared by grinding and then screening the excavated material. This preparation is complicated when the excavated material is very hard rock. Furthermore, this method of analysis requires sensitive equipment which is complex to handle and cannot be situated directly on the site because it is incompatible with the activity on a site (vibration, dust). The laboratory including this sensitive equipment is therefore generally situated far away from the site. This method of analysis therefore takes a long time and is complicated to perform. Furthermore, during this long analysis period, the excavated material must be stored on the sites which are very often located in highly restricted geographical areas (urban areas, mountain valleys).

There is therefore a need for a simpler and faster method for determining the lithological layer of an excavated material in order to determine if and how an excavated material can be valorised in order to optimize the ground area of sites, to avoid storage areas on the site and to allow a large amount of excavated material to be reliably valorised.

The Applicant has surprisingly found a method for analysing an excavated material which makes it possible to meet this need.

SUMMARY

According to a first aspect, the present invention relates to a method for identifying the lithological layer of an excavated material, comprising the following steps:
a) analysing a specimen of the excavated material using X-ray fluorescence spectroscopy in order to determine the mass concentration of each of the inorganic chemical elements contained in the said specimen,
step a) being performed on n different surfaces of the specimen in order to determine n mass concentrations of each of the inorganic chemical elements contained in the said specimen, with n being a whole number greater than or equal to 2, in particular between 3 and 20, more particularly between 5 and 15, and even more particularly 10,
b) calculating the mean of the n mass concentrations of each of the inorganic chemical elements contained in the said specimen and the standard deviation of this mean,
c) classifying each of the inorganic chemical elements contained in the excavated material according to the following criteria:
an inorganic chemical element with a mean of the n mass concentrations in the excavated material greater than 1% and a standard deviation of this mean less than 40% is classified as a homogeneous major inorganic chemical element,
an inorganic chemical element with a mean of the n mass concentrations in the excavated material greater than 1% and a standard deviation of this mean greater than 40% is classified as a dispersed major inorganic chemical element,
an inorganic chemical element with a mean of the n mass concentrations in the excavated material which lies between 0.01% and 1% and a standard deviation of this mean less than 40% is classified as a homogeneous minor inorganic chemical element,
an inorganic chemical element with a mean of the n mass concentrations in the excavated material which lies between 0.01% and 1% and a standard deviation of this mean greater than 40% is classified as a dispersed minor inorganic chemical element,
an inorganic chemical element with a mean of the n mass concentrations in the excavated material less than 0.01% and a standard deviation of this mean less than 40% is classified as a homogeneous trace inorganic chemical element, or
an inorganic chemical element with a mean of the n mass concentrations in the excavated material less than 0.01% and a standard deviation of this mean greater than 40% is classified as a dispersed trace inorganic chemical element, and
d) identifying the lithological layer of the excavated material based on the classification performed during step c).

Step a) of the analysis is advantageously very quick as it can be performed in just a few minutes.

Step a) is also very simple to perform. In particular, it does not require a step in which the specimen of the excavated material to be analysed is prepared.

This step a) of the analysis can also be performed directly on site in a mobile laboratory including a portable X-ray fluorescence spectrometer or an X-ray fluorescence spectrometer which is easily transported because it has a small size.

The mean of the n mass concentrations calculated by the analysis method of the invention makes it possible to reliably classify the inorganic chemical elements of the excavated material into major inorganic chemical elements, minor inorganic chemical elements, and trace inorganic chemical elements of the excavated material.

The standard deviation of this mean makes it possible to reliably classify the inorganic chemical elements of the excavated material according to their dispersibility.

Without wishing to be bound by any theory, the inventors believe that classifying the inorganic chemical elements of the excavated material into homogeneous or dispersed major inorganic chemical elements, homogeneous or dispersed minor inorganic chemical elements and homogeneous or dispersed trace inorganic chemical elements using the analysis method of the invention makes it possible to identify the lithological layer of the excavated material reliably, quickly and simply. The analysis method of the invention thus advantageously makes it possible to subsequently identify the lithological layer of an excavated material and then, depending on this identification, to decide if and how to valorise it.

Thus, according to another aspect, the present invention also relates to a method for valorising an excavated material which employs the identification method according to the invention, furthermore comprising the following step:
e) valorising the excavated material as a building material depending on the identification obtained in step d).

DETAILED DESCRIPTION

According to a first aspect, the present invention relates to a method for identifying the lithological layer of an excavated material, comprising the following steps:
a) analysing a specimen of the excavated material using X-ray fluorescence spectroscopy in order to determine the mass concentration of each of the inorganic chemical elements contained in the said specimen,
step a) being performed on n different surfaces of the specimen in order to determine n mass concentrations of each of the inorganic chemical elements contained in the said specimen, with n being a whole number greater than or equal to 2, in particular between 2 and 20, more particularly between 5 and 15, and even more particularly 10,
b) calculating the mean of the n mass concentrations of each of the inorganic chemical elements contained in the said specimen and the standard deviation of this mean,
c) classifying each of the inorganic chemical elements contained in the excavated material according to the following criteria:
an inorganic chemical element with a mean of the n mass concentrations in the excavated material greater than 1% and a standard deviation of this mean less than 40% is classified as a homogeneous major inorganic chemical element,
an inorganic chemical element with a mean of the n mass concentrations in the excavated material greater than 1% and a standard deviation of this mean greater than 40% is classified as a dispersed major inorganic chemical element,
an inorganic chemical element with a mean of the n mass concentrations in the excavated material which is between 0.01% and 1% and a standard deviation of this mean less than 40% is classified as a homogeneous minor inorganic chemical element,
an inorganic chemical element with a mean of the n mass concentrations in the excavated material which is between 0.01% and 1% and a standard deviation of this mean greater than 40% is classified as a dispersed minor inorganic chemical element,
an inorganic chemical element with a mean of the n mass concentrations in the excavated material less than 0.01% and a standard deviation of this mean less than 40% is classified as a homogeneous trace inorganic chemical element, or
an inorganic chemical element with a mean of the n mass concentrations in the excavated material less than 0.01% and a standard deviation of this mean greater than 40% is classified as a dispersed trace inorganic chemical element, and
d) identifying the lithological layer of the excavated material based on the classification performed during step c).

As used herein, "excavated material" (also called "excavation material") refers to any material which is the result of civil engineering or building work, be it in the Earth's surface, for example when digging trenches or creating foundations, or under the ground, for example when digging tunnels, caverns and mine galleries. The excavated material comprises, for example:
loose rock such as gravel, sand, silt, clay or mixtures thereof;
crushed rock;
material from previous constructions or from polluted sites such as polluted sites; or
mud.

For example, the excavated material is material extracted by a tunnel boring machine used to build an underground rail line, a train line or a road.

As used herein, "inorganic chemical elements" refers to the inorganic chemical elements from the following groups: alkali metals, alkaline earth metals, lanthanides, actinides, transition metals, post-transition metals, metalloids, non-metals and halogens, in particular alkaline earth metals, transition metals, post-transition metals, metalloids, non-metals and halogens. The inorganic chemical elements can typically be chosen from Ag, Al, As, Ba, Bi, Ca, Cd, Cl, Co, Cr, Cu, F, Fe, Hg, K, Mg, Mn, Mo, Ni, Nb, P, Pb, Rb, S, Sb, Se, Si, Sn, Sr, Ti, V, Zn and Zr, in particular chosen from Ag, Al, As, Ba, Bi, Ca, Cd, Cl, Co, Cr, Cu, Fe, K, Mg, Mn, Mo, Ni, Nb, P, Pb, Rb, S, Sb, Si, Sn Sr, Ti, V, Zn and Zr.

As used herein, "X-ray fluorescence spectroscopy" (also called "X-ray fluorescence spectrometry") refers to a technique for chemical analysis which uses a physical property of the substance, the X-ray fluorescence. The atoms all have a defined number of electrons and each of these electrons has a characteristic energy which is defined by its atomic level. The atomic levels correspond to an energy and can contain a precise number of electrons. The greater the amount of energy in an energy level, the more space there is but the lower the tendency of the electrons to fill it. An electron can be excited by a photon and change its energy level, moving to a higher energy level. The space left in the energy level by the electron is then filled by an electron from a different energy level. The transition between energy levels releases energy in different forms. The phenomenon of interest for X-ray fluorescence is the emission of a fluorescence photon in the X-ray range. The energy of each proton emitted in this way is known precisely for each element and the different possible transitions for an element are described. Tables therefore exist that give, for each element, all the possible emission energies and the minimum energy for exciting the atom. The spectrum obtained by X-ray fluorescence spectroscopy is characteristic of the specimen analysed.

According to one embodiment, analysis step a) can be performed directly on the surface of the excavated material, the specimen then being the excavated material, or on the surface of a sample of the excavated material, the specimen then being the sample.

According to one embodiment, analysis step a) using X-ray fluorescence spectroscopy can be performed with an energy varying from 0 to 100 keV, in particular from 0 to 50 keV, more particularly from 0 to 20 keV.

According to one particular embodiment, analysis step a) using X-ray fluorescence spectroscopy can be performed on one or more energy ranges, each energy range extending from −5 keV, in particular from −3 keV, more particularly from −2 keV of a central energy, to +5 keV, in particular to +3 keV, more particularly to +2 keV of the central energy, the central energy being the energy of a characteristic line of an inorganic chemical element contained in the specimen analysed.

Advantageously, performing the analysis using X-ray fluorescence spectroscopy on different energy ranges makes it possible to increase the signal received and hence increase the signal-to-noise ratio. Consequently, the inorganic chemical elements, in particular the inorganic polluting elements, contained in the specimen analysed are more easily detected and more easily measured.

Tables giving the central energy for each inorganic chemical element, in particular each inorganic polluting element, are known to a person skilled in the art.

According to one embodiment, the total acquisition time during analysis step a) using X-ray fluorescence spectroscopy can be 0.25 min to 10 min, in particular 0.5 to 5 min, more particularly 1 min to 3 min.

A total acquisition time within these ranges of values advantageously makes it possible to receive a high-quality signal and hence to improve the reliability of the determination of the mass concentration of each of the inorganic chemical elements contained in the specimen analysed.

Furthermore, the duration of the n analysis steps a) using X-ray fluorescence spectroscopy is advantageously much shorter than that of conventional X-ray diffraction analysis.

According to one embodiment, the analysis step a) using X-ray fluorescence spectroscopy can be performed with an acceleration voltage of the electron between 5 kV and 200 kV, in particular between 25 kV and 100 kV, and more particularly an acceleration voltage of the electron of 50 kV.

A value for the acceleration voltage within these ranges advantageously makes it possible to excite both the lightest inorganic chemical elements and the heaviest inorganic chemical elements, in particular inorganic polluting elements, contained in the specimen analysed. This therefore makes it possible to determine the mass concentration of each of the inorganic chemical elements, in particular inorganic polluting elements, contained in the specimen analysed.

X-ray fluorescence spectroscopy advantageously makes it possible to determine the mass concentration of each element of the specimen in less than ten minutes non-destructively and with no prior specimen preparation step such as drying, crushing and then possibly screening and pelleting.

According to one particular embodiment, the method according to the invention thus does not comprise a step in which the specimen of the excavated material is prepared, in particular one of the following preparation steps:
    a step in which the specimen is dried;
    a step in which the specimen is crushed and then possibly screened; and
    a step in which the specimen is made into pellets.

The mean of the n mass concentrations in the excavated material of each inorganic chemical element contained in the excavated material allows the said excavated material to be classified as a major inorganic chemical element, minor inorganic chemical element, or trace inorganic chemical element.

Typically, an inorganic chemical element:
    where the mean of the n mass concentrations in the excavated material is greater than 1% can be classified as a major inorganic chemical element,
    where the mean of the n mass concentrations in the excavated material is between 0.01% and 1% can be classified as a minor inorganic chemical element, or
    where the mean of the n mass concentrations in the excavated material is less than 0.01% can be classified as a trace inorganic chemical element.

For example, depending on the excavated material, Al, Ba, Ca, Fe, K, Mg, S and Si can be classified as a major inorganic chemical element, As, Cl, Cr, Cu, Mn, Ni, P, Rb, Sr, Ti, V, Zn and Zr can be classified as a minor inorganic chemical element and Ag, Bi, Cd, Co, Mo, Nb, Pb, Sb and Sn can be classified as a trace inorganic chemical element.

The standard deviation of the n mass concentrations in the excavated material of each inorganic chemical element contained in the excavated material allows the said excavated material to be classified according to its dispersibility, i.e. whether it is homogeneous or dispersed.

Typically, an inorganic chemical element:
    where the standard deviation of the mean of the n mass concentrations in the excavated material is less than 40% can be classified as a homogeneous inorganic chemical element, or
    where the standard deviation of the mean of the n mass concentrations in the excavated material is greater than 40% can be classified as a dispersed inorganic chemical element.

Classifying each inorganic chemical element contained in the excavated material into major, minor or trace inorganic chemical elements makes it possible to pre-identify the lithological layers depending on their chemical composition. The dispersibility of each inorganic chemical element contained in the excavated material then allows the lithological layer to be identified from the pre-identified lithological layers. This identification is performed by virtue of the structure of the lithological layer. Indeed, a lithological layer has a specific structure depending on the dispersibility of all or some of the inorganic chemical elements contained in the said lithological layer.

For example, the major elements Ba, Fe, K, Al, Si and Mg, the minor elements P, Ti, V, Cr, Ni and Zn and the trace elements Pb and Bi make it possible to pre-identify the lithological layers of Sapey gneiss GS and mica schists ξζ. If the major element Mg is homogeneous, then the lithological layer is Sapey gneiss GS. If the element Mg is dispersed, then the lithological layer is mica schists ξζ.

For example, the major elements Fe, Ti, Ca, K, Al, Si and Mg, the minor elements Ba, Zr, Rb, Cr, V and P and the trace elements Nb, Bi and Pb make it possible to pre-identify the lithological layers of sandstone schist or micaceous schists (phyllosilicates). If the trace element Bi is homogeneous, then the lithological layer is sandstone schists. If the trace element Bi is dispersed, then the lithological layer is micaceous schists (phyllosilicates).

The pre-identification and identification can be performed with the aid of geological maps and their associated explanatory notes or with the aid of geology books known to a person skilled in the art such as "Détermination des minéraux des roches au microscope polarisant" [Determining Minerals in Rocks using a Polarizing Microscope], by Marcel Roubault (published by Lamarre-Poinat).

The classification of each inorganic chemical element contained in the excavated material by virtue of the mean of the n mass concentrations and the standard deviation of this mean advantageously makes it possible to reliably identify the lithological layer of an excavated material.

Each lithological layer has known specific geomechanical and chemical properties. Their identification by the method according to the invention therefore makes it possible to conclude reliably, quickly and in accordance with the current recommendations whether the excavated material can be valorised as a building material and as what type of building material it can valorised, for example as backfill or aggregate.

Thus, according to another aspect, the present invention also relates to a method for valorising an excavated material which employs the identification method as defined above, furthermore comprising the following step:

e) valorising the excavated material as a building material depending on the identification obtained in step d).

The excavated material can be valorised as a building material if its lithological layer gives it geomechanical and chemical properties that are suitable for this valorisation. For example, these geomechanical and chemical properties can be:

an average sulphur content that is less than or equal to 0.45%, an average rock mass rating, or RMR, that is greater than or equal to 40, and a minimum value for the unconfined compressive strength, or UCS, that is greater than or equal to 2 MPa.

The average sulphur content can be determined by the analysis method of the present invention. The average rock mass rating can be determined according to the RMR89 system. The minimum value for the unconfined compressive strength can be determined according to the standard NF P94-420 (2000).

An excavated material with a lithological layer which gives it one of these geomechanical and chemical properties can undergo the valorisation step e). For example, the marly limestone jmCM, limestone tCd, dolomite tBD, sandstone hBo, mica schist AMD, mica schist AMF, Arpont mica schist Sv, quartzite rt, quartzite tQ, quartzite QSE and micaceous schist lithological layers give the excavated material one of these geomechanical and chemical properties.

Thus, an excavated material with a lithological layer that is limestone tCd, dolomite tBD, sandstone hBo, mica schist AMD, mica schist AMF, marly limestone jmCM, quartzite rt, quartzite tQ, quartzite QSE and micaceous schist is suitable for being valorised as a building material. It can therefore undergo the valorisation step e) of the valorisation method of the invention.

The geomechanical and chemical properties given to the excavated material by the lithological layer are known. A person skilled in the art can, for example, find this information in geotechnical studies on soil geomechanics in the databases published by the French Bureau de Recherches Géologiques et Minières (BRGM) (Bureau for Geological and Mining Research).

Typically, the building material can be backfill or aggregate, in particular backfill, aggregate for concrete or aggregate for asphalt.

As used herein, "backfill" refers to a building material intended to elevate a plot of land, fill a cavity or fill voids from mining activity.

As used herein, "aggregate" refers to a building material used to produce civil engineering structures, road works and buildings.

An aggregate for concrete and an aggregate for asphalt are examples of aggregate.

As used herein, "aggregate for asphalt" refers to an aggregate used to manufacture bitumen.

As used herein, "aggregate for concrete" refers to an aggregate used to manufacture concrete.

The valorisation step e) can comprise a step of producing a building material from the excavation material.

Typically, the production step can comprise one or more sub-steps of shaping the excavated material, the sub-step or sub-steps being adapted to the building material, in particular to backfill or aggregate, more particularly to backfill, aggregate for concrete or aggregate for asphalt.

An excavated material with a lithological layer which gives it the following geomechanical and chemical properties:

an average sulphur content that is less than or equal to 0.45%, an average rock mass rating that is greater than or equal to 40, and a minimum value for the unconfined compressive strength that is greater than or equal to 2 MPa is suitable for valorisation as backfill. This material can therefore undergo one or more sub-steps in which it is shaped suitably for backfill.

Typically, the marly limestone jmCM, limestone tCd, dolomite tBD, sandstone hBo, mica schist AMD, mica schist AMF, quartzite rt, quartzite tQ, quartzite QSE and micaceous schist lithological layers, and in particular mica schist AMD, give the excavated material the abovementioned properties.

Thus, an excavated material with a lithological layer which can be mica schist AMD, mica schist AMF, marly limestone jmCM, micaceous schist or mixtures thereof, in particular mica schist AMD, is suitable for valorisation as backfill. It can therefore undergo one or more sub-steps in which it is shaped suitably for backfill.

An excavated material with a lithological layer which gives it the following geomechanical and chemical properties:

an average sulphur content that is less than or equal to 0.45%, an average rock mass rating that is greater than or equal to 40, and a minimum value for the unconfined compressive strength that is greater than or equal to 2 MPa is suitable for valorisation as aggregate. This material can therefore undergo one or more steps in which it is shaped suitably for aggregate.

Typically, the limestone tCd, dolomite tBD, sandstone hBo, mica schist AMD, mica schist AMF, Arpont mica schist Av, quartzite rt, quartzite tQ, quartzite QSE lithological layers, and in particular quartzite rt and quartzite QSE, give the excavated material the abovementioned properties.

Thus, an excavated material with a lithological layer which can be limestone tCd, dolomite tBD, sandstone hBo, mica schist AMD, mica schist AMF, Arpont mica schist Sv, quartzite rt, quartzite tQ and quartzite QSE or mixtures thereof, in particular quartzite rt, quartzite QSE or a mixture thereof, is suitable for valorisation as aggregate. It can therefore undergo one or more sub-steps in which it is shaped suitably for aggregate.

An excavated material with a lithological layer which gives it the following geomechanical and chemical properties:
- an average sulphur content that is less than or equal to 0.45%,
- an average rock mass rating that is greater than or equal to 40, and
- a minimum value for the unconfined compressive strength that is greater than or equal to 2 MPa and less than or equal to 37 MPa is suitable for valorisation as aggregate for asphalt. This excavated material can therefore undergo one or more steps in which it is shaped suitably for aggregate for asphalt.

Typically, the limestone tCd, dolomite tBD, quartzite rt, quartzite tQ, quartzite QSE lithological layers, and in particular quartzite rt and quartzite QSE, give the excavated material the abovementioned properties.

Thus, an excavated material with a lithological layer which is limestone tCd, dolomite tBD, quartzite rt, quartzite tQ, quartzite QSE or mixtures thereof, in particular quartzite rt, quartzite QSE or a mixture thereof, is suitable for valorisation as aggregate for asphalt. It can therefore undergo one or more sub-steps in which it is shaped suitably for aggregate for asphalt.

An excavated material with a lithological layer which gives it the following geomechanical and chemical properties:
- an average sulphur content that is less than 0.25%,
- an average rock mass rating that is greater than or equal to 40, and
- a minimum value for the unconfined compressive strength that is greater than 2 MPa is suitable for valorisation as aggregate for concrete. This excavated material can therefore undergo one or more steps in which it is shaped suitably for aggregate for concrete.

Typically, the limestone tCd, dolomite tBD, sandstone hBo, mica schist AMD, mica schist AMF, Arpont mica schist Av, quartzite QSE and quartzite tQ lithological layers, and in particular limestone tCd, dolomite tBD, quartzite QSE and quartzite tQ, and more particularly quartzite tQ, give the excavated material the abovementioned properties.

Thus, an excavated material with a lithological layer which can be limestone tCd, dolomite tBD, sandstone hBo, mica schist AMD, mica schist AMF, Arpont mica schist Sv, quartzite QSE and quartzite tQ, and more particularly quartzite tQ, is suitable for valorisation as aggregate for concrete. It can therefore undergo one or more sub-steps in which it is shaped suitably for aggregate for concrete.

The shaping sub-step or sub-steps of the production method according to the invention are conventional steps which a person skilled in the art will be able to adapt to the excavated material and to the building material produced.

According to another aspect, the present invention also relates to an method for analysing an excavated material comprising the steps a) and b) as defined above.

According to another aspect, the present invention also relates to a method for valorising an excavated material which employs the analysis method as defined above and further comprising the steps c) and d) as defined above, and the valorisation step e) as defined above.

The invention will be described in more detail with the aid of the following examples which are given purely by way of illustration.

EXAMPLES

Example 1: Analysis of a First Excavated Material According to the Method of the Invention Ten different surfaces of a specimen of material excavated during the digging of a tunnel on the route of the Lyon-Turin rail line in the Vallée de Maurienne were analysed using X-ray fluorescence spectroscopy. No step in which the specimen is prepared was performed before the analysis.

The mean of the ten mass concentrations of each of the inorganic chemical elements contained in this specimen of excavated material and the standard deviation were determined.

The results are presented in Table 1 below.

TABLE 1

| Inorganic element | Mean of the ten mass concentrations (%) | Standard deviation (%) | |
| --- | --- | --- | --- |
| Ba | 0.01 | 37.5 | Homogeneous minor element |
| Zr | 0.004 | 64.22 | Dispersed trace element |
| Sr | 0.00005 | 301.51 | Dispersed trace element |
| Rb | 0.003 | 35.92 | Homogeneous trace element |
| Bi | 0.0002 | 301.51 | Dispersed trace element |
| As | 0.00006 | 301.51 | Dispersed trace element |
| Fe | 0.39 | 42.09 | Dispersed trace element |
| Mn | 0.003 | 301.51 | Dispersed trace element |
| Cr | 0.003 | 108.39 | Dispersed trace element |
| Ti | 0.05 | 47.13 | Dispersed minor element |
| Ca | 0.06 | 94.46 | Dispersed minor element |
| K | 2.16 | 42.71 | Dispersed major element |
| Al | 2.82 | 49.4 | Dispersed major element |
| Si | 34.44 | 31.8 | Homogeneous major element |
| Cl | 0.01 | 301.51 | Dispersed minor element |
| S | 0.02 | 181.76 | Dispersed minor element |
| Mg | 0.09 | 204.95 | Dispersed minor element |

The lithological layer of the excavated material is quartzite QSE. This accords with X-ray diffraction analysis carried out on a different specimen of the same excavated material. 30 minutes passed between the production of the excavated material and the result of the analysis using X-ray fluorescence spectroscopy. In contrast, over 5 days passed between the production of the excavated material and the result of the X-ray diffraction analysis.

This excavated material can be valorised as backfill or aggregate.

Example 2: Analysis of a Second Excavated Material According to the Method of the Invention Ten different surfaces of a specimen of material excavated during the digging of a tunnel on the route of the Lyon-Turin rail line in the Vallée de Maurienne were analysed using X-ray fluorescence spectroscopy. No step in which the specimen is prepared was performed before the analysis.

The mean of the ten mass concentrations of each of the inorganic chemical elements contained in this specimen of excavated material and the standard deviation were determined.

The results are presented in Table 2 below.

The lithological layer of the excavated material is Arpont mica schist Sv. This accords with X-ray diffraction analysis carried out on a different specimen of the same excavated material. 30 minutes passed between the production of the excavated material and the result of the analysis using X-ray fluorescence spectroscopy. In contrast, over 5 days passed between the production of the excavated material and the result of the X-ray diffraction analysis.

This excavated material can be valorised as aggregate for concrete.

Example 3: Analysis of a Third Excavated Material According to the Method of the Invention Ten different surfaces of a specimen of material excavated during the digging of a tunnel on the route of the Lyon-Turin rail line in the Vallée de Maurienne were analysed using X-ray fluorescence spectroscopy. No step in which the specimen is prepared was performed before the analysis.

The mean of the ten mass concentrations of each of the inorganic chemical elements contained in this specimen of excavated material and the standard deviation were determined.

The results are presented in Table 3 below.

The lithological layer of the excavated material is marly limestone jmCM. This accords with X-ray diffraction analysis carried out on a different specimen of the same excavated material. 30 minutes passed between the production of the excavated material and the result of the analysis using X-ray fluorescence spectroscopy. In contrast, over 5 days passed between the production of the excavated material and the result of the X-ray diffraction analysis.

This excavated material can be valorised as backfill.

TABLE 2

| Inorganic element | Mean of the ten mass concentrations (%) | Standard deviation (%) | |
|---|---|---|---|
| Ba | 0.15 | 42.86 | Dispersed minor element |
| Mo | 0.00004 | 316.23 | Dispersed trace element |
| Nb | 0.002 | 13.93 | Homogeneous trace element |
| Zr | 0.03 | 8.73 | Homogeneous minor element |
| Sr | 0.01 | 50.29 | Dispersed minor element |
| Rb | 0.02 | 9.83 | Homogeneous minor element |
| Bi | 0.001 | 40.17 | Dispersed trace element |
| As | 0.0006 | 116.3 | Dispersed trace element |
| Pb | 0.0005 | 93.07 | Dispersed trace element |
| Zn | 0.002 | 59.05 | Dispersed trace element |
| Cu | 0.004 | 55.45 | Dispersed trace element |

TABLE 2-continued

| Inorganic element | Mean of the ten mass concentrations (%) | Standard deviation (%) | |
|---|---|---|---|
| Fe | 2.05 | 33.89 | Homogeneous major element |
| Mn | 0.02 | 132.33 | Dispersed minor element |
| Cr | 0.01 | 33.54 | Homogeneous minor element |
| V | 0.01 | 24.79 | Homogeneous minor element |
| Ti | 0.66 | 31.1 | Homogeneous minor element |
| Ca | 0.25 | 71.82 | Dispersed minor element |
| K | 4.2 | 23.49 | Homogeneous major element |
| Al | 9.63 | 30.40 | Homogeneous major element |
| P | 0.02 | 97.15 | Dispersed minor element |
| Si | 20.85 | 29.7 | Homogeneous major element |
| S | 0.05 | 70.57 | Dispersed minor element |
| Mg | 0.44 | 109.79 | Dispersed minor element |

TABLE 3

| Inorganic element | Mean of the ten mass concentrations (%) | Standard deviation (%) | |
|---|---|---|---|
| Ba | 0.03 | 19.34 | Homogeneous minor element |
| Mo | 0.00003 | 316.23 | Dispersed trace element |
| Nb | 0.0001 | 133.36 | Dispersed trace element |
| Zr | 0.0001 | 87.71 | Dispersed trace element |
| Sr | 0.19 | 38.36 | Homogeneous minor element |
| Rb | 0.0002 | 106.98 | Dispersed trace element |
| As | 0.0002 | 131.71 | Dispersed trace element |
| Pb | 0.0007 | 109.49 | Dispersed trace element |
| Zn | 0.01 | 106.6 | Dispersed minor element |
| Cu | 0.0009 | 169.89 | Dispersed trace element |
| Ni | 0.0008 | 316.23 | Dispersed trace element |
| Fe | 0.37 | 60.67 | Dispersed minor element |
| Mn | 0.01 | 69.77 | Dispersed minor element |
| Cr | 0.01 | 46.22 | Dispersed minor element |
| V | 0.0002 | 316.23 | Dispersed trace element |
| Ti | 0.09 | 37.44 | Homogeneous minor element |
| Ca | 35 | 16.98 | Homogeneous major element |
| Al | 1.19 | 53 | Dispersed major element |
| K | 0.21 | 69.14 | Dispersed minor element |
| P | 0.02 | 75.01 | Dispersed minor element |
| Si | 7.71 | 43.40 | Dispersed major element |

TABLE 3-continued

| Inorganic element | Mean of the ten mass concentrations (%) | Standard deviation (%) | |
|---|---|---|---|
| Cl | 0.03 | 59.79 | Dispersed minor element |
| S | 0.17 | 26.27 | Homogeneous minor element |
| Mg | 0.10 | 316.23 | Dispersed minor element |

The invention claimed is:

1. A method for identifying a lithological layer of an excavated material, comprising the following steps:
   a) analysing a specimen of the excavated material using X-ray fluorescence spectroscopy in order to determine a mass concentration of each of inorganic chemical elements contained in the specimen,
   step a) being performed on n different surfaces of the specimen in order to determine n mass concentrations of each of the inorganic chemical elements contained in the specimen, with n being a whole number greater than or equal to 2,
   b) calculating a mean of the n mass concentrations of each of the inorganic chemical elements contained in the specimen and a standard deviation of the mean,
   c) classifying each of the inorganic chemical elements contained in the excavated material according to the following criteria:
       the inorganic chemical element with the mean of the n mass concentrations in the excavated material greater than 1% and the standard deviation of the mean less than 40% is classified as a homogeneous major inorganic chemical element,
       the inorganic chemical element with the mean of the n mass concentrations in the excavated material greater than 1% and the standard deviation of the mean greater than 40% is classified as a dispersed major inorganic chemical element,
       the inorganic chemical element with the mean of the n mass concentrations in the excavated material which is between 0.01% and 1% and the standard deviation of the mean less than 40% is classified as a homogeneous minor inorganic chemical element,
       the inorganic chemical element with the mean of the n mass concentrations in the excavated material which is between 0.01% and 1% and a standard deviation of the mean greater than 40% is classified as a dispersed minor inorganic chemical element,
       the inorganic chemical element with the mean of the n mass concentrations in the excavated material less than 0.01% and the standard deviation of the mean less than 40% is classified as a homogeneous trace inorganic chemical element, or
       the inorganic chemical element with the mean of the n mass concentrations in the excavated material less than 0.01% and the standard deviation of the mean greater than 40% is classified as a dispersed trace inorganic chemical element, and
   d) identifying the lithological layer of the excavated material based on the classification performed during step c).

2. The method according to claim 1, in which the excavated material is material extracted by a tunnelling machine used to build an underground rail line, a train line or a road.

3. The method according claim 1, in which the inorganic chemical elements are chosen from Ag, Al, As, Ba, Bi, Ca, Cd, Cl, Co, Cr, Cu, F, Fe, Hg, K, Mg, Mn, Mo, Ni, Nb, P, Pb, Rb, S, Sb, Se, Si, Sn, Sr, Ti, V, Zn and Zr.

4. The method according to claim 1, not comprising a step in which the specimen of the excavated material is prepared.

5. A method for valorising an excavated material which employs the identification method as defined in claim 1, furthermore comprising the following step:
   e) valorising the excavated material as a building material depending on the identification obtained in step d).

6. The method according to claim 5, in which the building material is backfill or aggregate.

7. The method according to claim 5, in which the valorisation step e) comprises a step of producing a building material from the excavation material.

8. The method according to claim 7, in which the production step comprises one or more sub-steps of shaping the excavated material, the one or more sub-steps being adapted to the building material.

9. The method according to claim 8, in which the lithological layer of the excavated material gives the excavated material the following geomechanical and chemical properties:
   an average sulphur content that is less than or equal to 0.45%,
   an average rock mass rating that is greater than or equal to 40, and
   a minimum value for an unconfined compressive strength that is greater than or equal to 2 MPa
undergoes one or more sub-steps in which it is shaped suitably for backfill.

10. The method according to claim 9, in which the lithological layer of the excavated material is mica schist AMD, mica schist AMF, marly limestone jmCM, micaceous schist, or mixtures thereof.

11. The method according to claim 8, in which the lithological layer of the excavated material gives the excavated material the following geomechanical and chemical properties:
   an average sulphur content that is less than or equal to 0.45%,
   an average rock mass rating that is greater than or equal to 40, and
   a minimum value for the unconfined compressive strength that is greater than or equal to 2 MPa
undergoes one or more sub-steps in which it is shaped suitably for aggregate.

12. The method according to claim 11, in which the lithological layer of the excavated material is limestone tCd, dolomite tBD, sandstone hBo, mica schist AMD, mica schist AMF, quartzite rt, quartzite tQ and quartzite QSE or mixtures thereof.

* * * * *